United States Patent
Porta Garcia et al.

(10) Patent No.: US 9,640,839 B2
(45) Date of Patent: May 2, 2017

(54) OXIRANYL ESTER DERIVATIVES AS ADDITIVE FOR ELECTROLYTES IN LITHIUM ION BATTERIES

(71) Applicant: BASF SE, Ludwigshafen (DE)

(72) Inventors: Marta Porta Garcia, Mannheim (DE); Frederick Francois Chesneau, St. Leon-Rot (DE); Michael Schmidt, Seeheim-Jugenheim (DE); Dominic Riedel, Mannheim (DE); Denis Schroeder, Ludwigshafen (DE); Joaquim Henrique Teles, Waldsee (DE); Arnd Garsuch, Ludwigshafen (DE); Stefan Herzog, Lambrecht (DE); Axel Kirste, Limburgerhof (DE); Patrick Krieg, Ludwigshafen (DE); Christian Karcher, Boehl-Iggelheim (DE); Nicolas Vautravers, Strasbourg (FR); Stefano Meini, Munich (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/907,954

(22) PCT Filed: Jul. 11, 2014

(86) PCT No.: PCT/EP2014/064970
§ 371 (c)(1),
(2) Date: Jan. 27, 2016

(87) PCT Pub. No.: WO2015/010931
PCT Pub. Date: Jan. 29, 2015

(65) Prior Publication Data
US 2016/0172709 A1    Jun. 16, 2016

(30) Foreign Application Priority Data

Jul. 23, 2013   (EP) .................................. 13177603
May 6, 2014    (EP) .................................. 14167189

(51) Int. Cl.
*H01M 10/0525*   (2010.01)
*H01M 10/0567*   (2010.01)
*H01M 10/0568*   (2010.01)
*H01M 10/0569*   (2010.01)
*C07D 303/12*    (2006.01)
*C07D 303/16*    (2006.01)
*C07D 303/17*    (2006.01)
*C07D 303/22*    (2006.01)
*C07D 303/30*    (2006.01)

(52) U.S. Cl.
CPC ... H01M 10/0567 (2013.01); H01M 10/0525 (2013.01); H01M 10/0568 (2013.01); H01M 10/0569 (2013.01); *C07D 303/12* (2013.01); *C07D 303/16* (2013.01); *C07D 303/17* (2013.01); *C07D 303/22* (2013.01); *C07D 303/30* (2013.01); *H01M 2300/0025* (2013.01); *H01M 2300/0042* (2013.01)

(58) Field of Classification Search
CPC ......... H01M 10/0525; H01M 10/0566; H01M 10/0567; H01M 10/0568; H01M 10/0569
See application file for complete search history.

(56) References Cited

U.S. PATENT DOCUMENTS

| | | | |
|---|---|---|---|
| 6,413,678 B1 | 7/2002 | Hamamoto et al. | |
| 2006/0147809 A1* | 7/2006 | Amine | H01M 10/0567 429/326 |
| 2009/0035656 A1 | 2/2009 | Lee et al. | |
| 2009/0191455 A1* | 7/2009 | Gao | H01M 10/0525 429/149 |
| 2009/0191457 A1 | 7/2009 | Sano | |
| 2015/0079483 A1* | 3/2015 | Cresce | C07F 9/65505 429/338 |

FOREIGN PATENT DOCUMENTS

| | | |
|---|---|---|
| EP | 0 683 587 A1 | 11/1995 |
| JP | 2012-216390 A | 11/2012 |
| JP | 2013-137873 A | 7/2013 |
| KR | 2008-0101163 A | 11/2008 |
| KR | 2008-0110162 A | 12/2008 |

OTHER PUBLICATIONS

U.S. Appl. No. 14/906,471, filed Jan. 20, 2016, Marta Porta Garcia, et al.
International Search Report and Written Opinion issued Oct. 8, 2014 in PCT/EP2014/064970 filed Jul. 11, 2014 (reference previously filed, submitting additional pages).
E. Markevich, et al., "Reasons for capacity fading of $LiCoPO_4$ cathodes in $LiPF_6$ containing electrolyte solutions" Electrochemistry Communications, vol. 15, 2012, pp. 22-25.
Ran Elazari, et al., "Rechargeable lithiated silicon-sulfur (SLS) battery prototypes" Electrochemistry Communications, vol. 14, 2012, pp. 21-24.
A. A. Bredikhin, et al., "New reaction of glycidols with oxalyl chloride and phosgene—an approach to cyclic esters" Russian Chemical Bulletin, vol. 48, No. 11, Nov. 1999, pp. 2086-2090 and Cover Page.
International Search Report and Written Opinion of the International Searching Authority Issued Oct. 8, 2014, in PCT/EP2014/064970 Filed Jul. 11, 2014.

* cited by examiner

*Primary Examiner* — Anca Eoff
(74) *Attorney, Agent, or Firm* — Oblon, McClellend, Maier & Neustadt, L.L.P.

(57) ABSTRACT

The present invention relates to an electrolyte composition (A) containing (i) at least one aprotic organic solvent; (ii) at least one conducting salt; (iii) at least one compound of formula (I) and (iv) optionally at least one further additive.

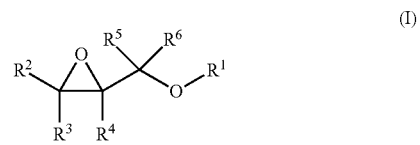

12 Claims, No Drawings

OXIRANYL ESTER DERIVATIVES AS ADDITIVE FOR ELECTROLYTES IN LITHIUM ION BATTERIES

The present invention relates to an electrolyte composition (A) containing
(i) at least one aprotic organic solvent;
(ii) at least one conducting salt;
(iii) at least one compound of formula (I)

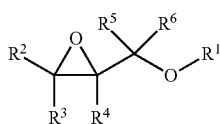

wherein
$R^1$, $R^2$, $R^3$, $R^4$, $R^5$, and $R^6$ are defined below, and
(iv) optionally at least one further additive.

The present invention further relates to the use of compounds of formula (I) as additives for electrolytes in electrochemical cells and to electrochemical cells comprising the above described electrolyte composition (A), at least one cathode (B) comprising at least one cathode active material, and at least one anode (C) comprising at least one anode active material.

Storing electrical energy is a subject of still growing interest. Efficient storage of electric energy would allow electric energy to be generated when it is advantageous and used when needed.

Accumulators, for example lead accumulators and nickel-cadmium accumulators, have been known for many decades. The known lead accumulators and nickel-cadmium accumulators have the disadvantages, however, of a comparatively low energy density and of a memory effect which reduces the rechargeability and hence the useful life of lead accumulators and nickel-cadmium accumulators.

Lithium ion accumulators, frequently also referred to as lithium ion batteries, are used as an alternative. They provide higher energy densities than accumulators based on lead or comparatively noble heavy metals.

Since many lithium ion batteries utilize metallic lithium or lithium in oxidation state 0, or produce it as an intermediate, they are water sensitive. Moreover, the conductive salts used, for example $LiFP_6$, are water sensitive during long-term operation. Water is therefore not a usable solvent for the lithium salts used in lithium ion batteries. Instead, organic carbonates, ethers, esters and ionic liquids are used as sufficiently polar solvents. Most state of the art lithium ion batteries in general comprise not a single solvent but a solvent mixture of different organic aprotic solvents. During charge and discharge of lithium ion batteries various reactions take place at different cell potentials. It is known that during the first charging process of a lithium ion battery usually a film is formed on the anode. This film is often called solid electrolyte interface (SEI). The SEI is permeable for lithium ions and protects the electrolyte from direct contact with the anode and vice versa. It is formed by reductive decomposition of components of the electrolyte composition like solvents, e.g. carbonates, esters, and ethers, and conductive salts on the surface of the anode, especially if the anode active material is a carbonaceous material like graphite. A certain amount of the lithium present in the cell is irreversibly consumed for the formation of the SEI and cannot be replaced. One possibility to reduce the amount of irreversibly consumed lithium is the addition of suitable chemical compounds which are easily decomposed on the anode by reduction and thereby forming a film on the surface of the anode. One especially well suited compound is vinylene carbonate, see for instance EP 0 683 587 B1 and U.S. Pat. No. 6,413,678 B1. Vinylene carbonate forms a stable SEI on a graphite anode in lithium ion batteries.

Other film forming additives are known, inter alia oxiranyl derivatives as described in US 2009/0035656 A1 disclosing glycidyl ether compounds as film forming additives for electrolytes of lithium batteries.

Nevertheless there is still the need for enhancing the lifetime of secondary batteries and a demand for electrolyte additives leading to a prolonged life time and cycle stability of secondary electrochemical cells.

It was an object of the present invention to provide an electrolyte composition leading to an improved lifetime of electrochemical cells, in particular lithium ion batteries. A further object of the present invention was to provide electrochemical cells, in particular lithium ion batteries of high energy density and/or higher operating voltage having good performance characteristics and long lifetime.

This object is achieved by an electrolyte composition (A) containing
(i) at least one aprotic organic solvent;
(ii) at least one conducting salt;
(iii) at least one compound of formula (I)

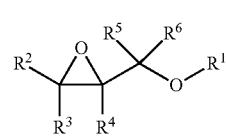

wherein
$R^1$ is selected from $C(O)OR^7$, $C(O)C(O)OR^7$, $S(O)_2R^7$, $S(O)_2OR^7$, $(CH_2)_sSO_2(CH_2)_sR^7$, $P(O)(OR^7)R^7$, and $P(O)(OR^7)_2$;
$R^2$ is selected from H, F, $C_1$-$C_6$ alkyl, $C_3$-$C_6$ (hetero)cycloalkyl, $C_2$-$C_6$ alkenyl, $C_3$-$C_6$ (hetero)cycloalkenyl, $C_2$-$C_6$ alkynyl, $C_5$-$C_7$ (hetero)aryl, $C_6$-$C_{13}$ aralkyl, wherein alkyl, (hetero)cycloalkyl, aralkyl, alkenyl, (hetero)cycloalkenyl, alkynyl, and (hetero)aryl may be substituted by one or more substituents selected from F, CN, $C_1$-$C_6$ alkyl, $C_3$-$C_6$ (hetero)cycloalkyl, $C_2$-$C_6$ alkenyl, $C_5$-$C_7$ (hetero)aryl, $OR^8$, $C(O)R^8$, $C(O)OR^8$, $OC(O)R^8$, $OC(O)OR^8$, $OC(O)C(O)OR^8$, $S(O)_2OR^8$ and $OS(O)_2R^8$;
$R^3$ and $R^4$ are independently from each other selected from H, F, $C_1$-$C_6$ alkyl, $C_3$-$C_6$ (hetero)cycloalkyl, $C_2$-$C_6$ alkenyl, $C_3$-$C_6$ (hetero)cycloalkenyl, $C_2$-$C_6$ alkynyl, $C_5$-$C_7$ (hetero)aryl, $C_6$-$C_{13}$ aralkyl, wherein alkyl, (hetero)cycloalkyl, alkenyl, (hetero)cycloalkenyl, alkynyl, (hetero)aryl, and aralkyl, may be substituted by one or more substituents selected from F, CN, and optionally fluorinated oxiranyl;
$R^5$ and $R^6$ are independently from each other selected from H, $C_1$-$C_6$ alkyl, $C_3$-$C_6$ (hetero)cycloalkyl, $C_2$-$C_6$ alkenyl, $C_3$-$C_6$ (hetero)cycloalkenyl, $C_2$-$C_6$ alkynyl, $C_5$-$C_7$ (hetero)aryl, $C_6$-$C_{13}$ aralkyl, wherein alkyl, (hetero)cycloalkyl, aralkyl, alkenyl, (hetero)cycloalkenyl, alkynyl, and (hetero)aryl may be substituted by one or more substituents selected from F, CN, and optionally fluorinated oxiranyl;

R⁷ is selected from $C_1$-$C_6$ alkyl, $C_3$-$C_6$ (hetero)cycloalkyl, $C_2$-$C_6$ alkenyl, $C_3$-$C_6$ (hetero)cycloalkenyl, $C_2$-$C_6$ alkynyl, $C_5$-$C_7$ (hetero)aryl, and $C_6$-$C_{13}$ aralkyl, wherein alkyl, (hetero)cycloalkyl, aralkyl, alkenyl, (hetero)cycloalkenyl, alkynyl, and (hetero)aryl may be substituted by one or more substituents selected from F, CN, $C_1$-$C_6$ alkyl, $C_2$-$C_6$ alkenyl, $C_5$-$C_7$ (hetero)aryl, $OR^9$, $OC(O)R^9$, $C(O)R^9$, $C(O)OR^9$, $OC(O)OR^9$, $OC(O)C(O)OR^9$, $S(O)_2OR^9$, $OS(O)_2R^9$, and $C_3$-$C_6$ (hetero)cycloalkyl which may be substituted by one or more substituents selected from $C_1$-$C_6$ alkyl, $C_3$-$C_6$ (hetero)cycloalkyl, $C_2$-$C_6$ alkenyl, $C_3$-$C_6$ (hetero)cycloalkenyl, $C_2$-$C_6$ alkynyl, $C_5$-$C_7$ (hetero)aryl, $C_6$-$C_{13}$ aralkyl, wherein alkyl, (hetero)cycloalkyl, aralkyl, alkenyl, (hetero)cycloalkenyl, alkynyl, and (hetero)aryl may be substituted by one or more substituents selected from F, CN, and optionally fluorinated oxiranyl;

$R^8$ and $R^9$ are independently from each other selected from H, $C_1$-$C_6$ alkyl, $C_3$-$C_6$ (hetero)cycloalkyl, $C_2$-$C_6$ alkenyl, $C_3$-$C_6$ (hetero)cycloalkenyl, $C_2$-$C_6$ alkynyl, $C_5$-$C_7$ (hetero)aryl, $C_6$-$C_{13}$ aralkyl, wherein alkyl, (hetero)cycloalkyl, aralkyl, alkenyl, (hetero)cycloalkenyl, alkynyl, and (hetero)aryl may be substituted by one or more substituents selected from F, CN, and optionally fluorinated oxiranyl;

s and t are independently from each other 1, 2 or 3; and (iv) optionally at least one further additive.

The problem is further solved by the use of at least one compound of formula (I) as additive for electrolytes in electrochemical cells; and by the electrochemical cell comprising the electrolyte composition (A) as described above, at least one cathode (B) comprising at least one cathode active material, and at least one anode (C) comprising at least one anode active material.

The compounds of general formula (I) show high reduction potentials indicating their suitability as additives forming a film on the anode of secondary electrochemical cells. Electrolytes for lithium ion secondary batteries comprising at least one aprotic organic solvent or a mixture thereof, at least one conducting salt leads and at least one compound of general formula (I) show good values of the internal resistance and very small decrease of capacity retention during cycling.

The inventive electrolyte composition (A) is preferably liquid at working conditions; more preferred it is liquid at 1 bar and 25° C., even more preferred the electrolyte composition is liquid at 1 bar and -15° C., in particular the electrolyte composition is liquid at 1 bar and -30° C., even more preferred the electrolyte composition is liquid at 1 bar and −50° C.

The electrolyte composition (A) contains at least one aprotic organic solvent (i), preferably at least two aprotic organic solvents (i). According to one embodiment the electrolyte composition (A) may contain up to ten aprotic organic solvents (i).

The at least one aprotic organic solvent (i) is preferably selected from (a) cyclic and acyclic organic carbonates, which may be partly halogenated, (b) di-$C_1$-$C_{10}$-alkylethers, which may be partly halogenated, (c) di-$C_1$-$C_4$-alkyl-$C_2$-$C_6$-alkylene ethers and polyethers, which may be partly halogenated, (d) cyclic ethers, which may be partly halogenated, (e) cyclic and acyclic acetales and ketales, which may be partly halogenated, (f) ortho esters, which may be partly halogenated, (g) cyclic and acyclic esters of carboxylic acids, which may be partly halogenated, (h) cyclic and acyclic sulfones, which may be partly halogenated, (i) cyclic and acyclic nitriles and dinitriles, which may be partly halogenated, and (j) ionic liquids, which may be partly halogenated.

More preferred the at least one aprotic organic solvent (i) is selected from cyclic and acyclic organic carbonates (a), di-$C_1$-$C_{10}$-alkylethers (b), di-$C_1$-$C_4$-alkyl-$C_2$-$C_6$-alkylene ethers and polyethers (c) and cyclic and acyclic acetales and ketales (e), even more preferred electrolyte composition (A) contains at least one aprotic organic solvent (i) selected from cyclic and acyclic organic carbonates (a) and most preferred electrolyte composition (A) contains at least two aprotic organic solvents (i) selected from cyclic and acyclic organic carbonates (a), in particular preferred electrolyte composition (A) contains at least one aprotic solvent (i) selected from cyclic organic carbonates and at least one aprotic organic solvent (i) selected from acyclic organic carbonates.

The aprotic organic solvents (a) to (j) may be partly halogenated, e.g. they may be partly fluorinated, partly chlorinated or partly brominated, preferably they may be partly fluorinated. "Partly halogenated" means, that one or more H of the respective molecule is substituted by a halogen atom, e.g. by F, Cl or Br. Preference is given to the substitution by F. The at least one solvent (i) may be selected from partly halogenated and non-halogenated aprotic organic solvents (a) to (j), i.e. the electrolyte composition may contain a mixture of partly halogenated and non-halogenated aprotic organic solvents.

Examples of suitable organic carbonates (a) are cyclic organic carbonates according to the general formula (a1), (a2) or (a3)

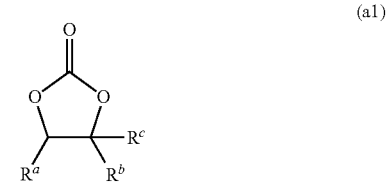

(a1)

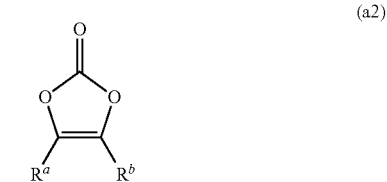

(a2)

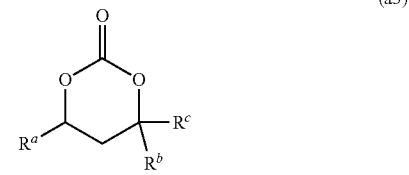

(a3)

wherein $R^a$, $R^b$ and $R^c$ being different or equal and being independently from each other selected from hydrogen; $C_1$-$C_4$-alkyl, preferably methyl; F; and $C_1$-$C_4$-alkyl substituted by one or more F, e.g. $CF_3$.

"$C_1$-$C_4$-alkyl" is intended to include methyl, ethyl, n-propyl, iso-propyl, n-butyl, iso-butyl, sec.-butyl and tert.-butyl.

Preferred cyclic organic carbonates (a) are of general formula (a1), (a2) or (a3) wherein $R^a$, $R^b$ and $R^c$ are H. Examples are ethylene carbonate, vinylene carbonate, and propylene carbonate. A preferred cyclic organic carbonate (a) is ethylene carbonate. Further preferred cyclic organic carbonates (a) are difluoroethylene carbonate (a4) and monofluoroethylene carbonate (a5)

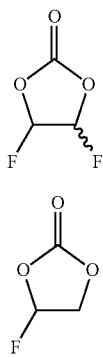

Examples of suitable acyclic organic carbonates (a) are dimethyl carbonate, diethyl carbonate, methylethyl carbonate and mixtures thereof.

In one embodiment of the invention the electrolyte composition (A) contains mixtures of acyclic organic carbonates (a) and cyclic organic carbonates (a) at a ratio by weight of from 1:10 to 10:1, preferred of from 3:1 to 1:1.

Examples of suitable acyclic di-$C_1$-$C_{10}$-alkylethers (b) are dimethylether, ethylmethylether, diethylether, diisopropylether, and di-n-butylether.

Examples of di-$C_1$-$C_4$-alkyl-$C_2$-$C_6$-alkylene ethers (c) are 1,2-dimethoxyethane, 1,2-diethoxyethane, diglyme (diethylene glycol dimethyl ether), triglyme (triethyleneglycol dimethyl ether), tetraglyme (tetraethyleneglycol dimethyl ether), and diethylenglycoldiethylether.

Examples of suitable polyethers (c) are polyalkylene glycols, preferably poly-$C_1$-$C_4$-alkylene glycols and especially polyethylene glycols. Polyethylene glycols may comprise up to 20 mol % of one or more $C_1$-$C_4$-alkylene glycols in copolymerized form. Polyalkylene glycols are preferably dimethyl- or diethyl-end-capped polyalkylene glycols. The molecular weight $M_w$ of suitable polyalkylene glycols and especially of suitable polyethylene glycols may be at least 400 g/mol. The molecular weight $M_w$ of suitable polyalkylene glycols and especially of suitable polyethylene glycols may be up to 5 000 000 g/mol, preferably up to 2 000 000 g/mol.

Examples of suitable cyclic ethers (d) are tetrahydrofurane and 1,4-dioxane.

Examples of suitable acyclic acetals (e) are 1,1-dimethoxymethane and 1,1-diethoxymethane. Examples for suitable cyclic acetals (e) are 1,3-dioxane and 1,3-dioxolane.

Examples of suitable ortho esters (f) are tri-$C_1$-$C_4$ alkoxy methane, in particular trimethoxymethane and triethoxymethane. Examples of suitable cyclic ortho esters (f) are 1,4-dimethyl-3,5,8-trioxabicyclo[2.2.2]octane and 4-ethyl-1-methyl-3,5,8-trioxabicyclo[2.2.2]octane.

Examples of suitable acyclic esters of carboxylic acids (g) are ethyl acetate, methyl butanoate, and esters of dicarboxylic acids like 1,3-dimethyl propanedioate. An example of a suitable cyclic ester of carboxylic acids (lactones) is γ-butyrolactone.

Examples of suitable cyclic and acyclic sulfones (h) are ethyl methyl sulfone, dimethyl sulfone, and tetrahydrothiophene-S,S-dioxide.

Examples of suitable cyclic and acyclic nitriles and dinitriles (i) are adipodinitrile, acetonitrile, propionitrile, butyronitrile.

The water content of the inventive electrolyte composition is preferably below 100 ppm, based on the weight of the electrolyte composition, more preferred below 50 ppm, most preferred below 30 ppm. The water content may be determined by titration according to Karl Fischer, e.g. described in detail in DIN 51777 or ISO760: 1978.

The content of HF of the inventive electrolyte composition is preferably below 60 ppm, based on the weight of the electrolyte composition, more preferred below 40 ppm, most preferred below 20 ppm. The HF content may be determined by titration according to potentiometric or potentiographic titration method.

The inventive electrolyte composition (A) furthermore contains at least one conducting salt (ii). Electrolyte composition (A) functions as a medium that transfers ions participating in the electrochemical reaction taking place in an electrochemical cell. The conducting salt(s) (ii) present in the electrolyte are usually solvated in the aprotic organic solvent(s) (i). Preferably the conducting salt (ii) is a lithium salt. The conducting salt is preferably selected from the group consisting of Li[F$_{6-x}$P(C$_y$F$_{2y+1}$)$_x$], wherein x is an integer in the range from 0 to 6 and y is an integer in the range from 1 to 20;

Li[B(R$^I$)$_4$], Li[B(R$^I$)$_2$(OR$^{II}$O)] and Li[B(OR$^{II}$O)$_2$] wherein each R$^I$ is independently from each other selected from F, Cl, Br, I, C$_1$-C$_4$ alkyl, C$_2$-C$_4$ alkenyl, and C$_2$-C$_4$ alkynyl, wherein alkyl, alkenyl, and alkynyl may be substituted by one or more OR$^{III}$, wherein R$^{III}$ is selected from C$_1$-C$_6$ alkyl, C$_2$-C$_6$ alkenyl, and C$_2$-C$_6$ alkynyl, and (OR$^{II}$O) is a bivalent group derived from a 1,2- or 1,3-diol, a 1,2- or 1,3-dicarboxlic acid or a 1,2- or 1,3-hydroxycarboxylic acid, wherein the bivalent group forms a 5- or 6-membered cycle via the both oxygen atoms with the central B-atom;

LiClO$_4$; LiAsF$_6$; LiCF$_3$SO$_3$; Li$_2$SiF$_6$; LiSbF$_6$; LiAlCl$_4$; Li[N(SO$_2$F)$_2$]; lithium tetrafluoro (oxalato) phosphate; lithium oxalate; and salts of the general formula Li[Z(C$_n$F$_{2n+1}$SO$_2$)$_m$], where m and n are defined as follows:
 m=1 when Z is selected from oxygen and sulfur,
 m=2 when Z is selected from nitrogen and phosphorus,
 m=3 when Z is selected from carbon and silicon, and
 n is an integer in the range from 1 to 20.

Suited 1,2- and 1,3-diols from which the bivalent group (OR$^{II}$O) is derived may be aliphatic or aromatic and may be selected, e.g., from 1,2-dihydroxybenzene, propane-1,2-diol, butane-1,2-diol, propane-1,3-diol, butan-1,3-diol, cyclohexyl-trans-1,2-diol and naphthalene-2,3-diol which are optionally are substituted by one or more F and/or by at least one straight or branched non fluorinated, partly fluorinated or fully fluorinated C$_1$-C$_4$ alkyl group. An example for such 1,2- or 1,3-diole is 1,1,2,2-tetra(trifluoromethyl)-1,2-ethane diol.

"Fully fluorinated C$_1$-C$_4$ alkyl group" means, that all H-atoms of the alkyl group are substituted by F.

Suited 1,2- or 1,3-dicarboxlic acids from which the bivalent group (OR$^{II}$O) is derived may be aliphatic or aromatic, for example oxalic acid, malonic acid (propane-1,3-dicarboxylic acid), phthalic acid or isophthalic acid, preferred is oxalic acid. The 1,2- or 1,3-dicarboxlic acid are optionally substituted by one or more F and/or by at least one straight or branched non fluorinated, partly fluorinated or fully fluorinated $C_1$-$C_4$ alkyl group.

Suited 1,2- or 1,3-hydroxycarboxylic acids from which the bivalent group ($OR^{II}O$) is derived may be aliphatic or aromatic, for example salicylic acid, tetrahydro salicylic acid, malic acid, and 2-hydroxy acetic acid, which are optionally substituted by one or more F and/or by at least one straight or branched non fluorinated, partly fluorinated or fully fluorinated $C_1$-$C_4$ alkyl group. An example for such 1,2- or 1,3-hydroxycarboxylic acids is 2,2-bis(trifluoromethyl)-2-hydroxy-acetic acid.

Examples of $Li[B(R^I)_4]$, $Li[B(R^I)_2(OR^{II}O)]$ and $Li[B(OR^{II}O)_2]$ are $LiBF_4$, lithium difluoro oxalato borate and lithium dioxalato borate.

Preferably the at least one conducting salt (ii) is selected from $LiPF_6$, $LiBF_4$, and $LiPF_3(CF_2CF_3)_3$, more preferred the conducting salt (ii) is selected from $LiPF_6$ and $LiBF_4$, and the most preferred conducting salt (ii) is $LiPF_6$.

The at least one conducting salt (ii) is usually present at a minimum concentration of at least 0.01 wt.-%, preferably of at least 1 wt.-%, and more preferred of at least 5 wt.-%, based on the total weight of the electrolyte composition. Usually the upper concentration limit for the at least one conducting salt (ii) is 25 wt.-%, based on the total weight of the electrolyte composition.

The inventive electrolyte composition (A) contains as component (iii) at least one compound of formula (I)

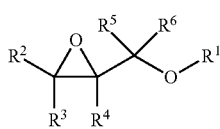

(I)

wherein
$R^1$ is selected from $C(O)OR^7$, $C(O)C(O)OR^7$, $S(O)_2R^7$, $S(O)_2OR^7$, $(CH_2)_sSO_2(CH_2)_tR^7$, $P(O)(OR^7)R^7$, and $P(O)(OR^7)_2$; preferably $R^1$ is selected from $C(O)OR^7$, $C(O)C(O)OR^7$, $S(O)_2R^7$, $S(O)_2OR^7$, $P(O)(OR^7)R^7$, and $P(O)(OR^7)_2$;
$R^2$ is selected from H, F, $C_1$-$C_6$ alkyl, $C_3$-$C_6$ (hetero)cycloalkyl, $C_2$-$C_6$ alkenyl, $C_3$-$C_6$ (hetero)cycloalkenyl, $C_2$-$C_6$ alkynyl, $C_5$-$C_7$ (hetero)aryl, $C_6$-$C_{13}$ aralkyl, wherein alkyl, (hetero)cycloalkyl, aralkyl, alkenyl, (hetero)cycloalkenyl, alkynyl, and (hetero)aryl may be substituted by one or more substituents selected from F, CN, $C_1$-$C_6$ alkyl, $C_3$-$C_6$ (hetero)cycloalkyl, $C_2$-$C_6$ alkenyl, $C_5$-$C_7$ (hetero)aryl, $OR^8$, $C(O)R^8$, $C(O)OR^8$, $OC(O)R^8$, $OC(O)OR^8$, $OC(O)C(O)OR^8$, $S(O)_2OR^8$ and $OS(O)_2R^8$;
$R^3$ and $R^4$ are independently from each other selected from H, F, $C_1$-$C_6$ alkyl, $C_3$-$C_6$ (hetero)cycloalkyl, $C_2$-$C_6$ alkenyl, $C_3$-$C_6$ (hetero)cycloalkenyl, $C_2$-$C_6$ alkynyl, $C_5$-$C_7$ (hetero)aryl, $C_6$-$C_{13}$ aralkyl, wherein alkyl, (hetero)cycloalkyl, alkenyl, (hetero)cycloalkenyl, alkynyl, (hetero)aryl, and aralkyl, may be substituted by one or more substituents selected from F, CN, and optionally fluorinated oxiranyl;
$R^5$ and $R^6$ are independently from each other selected from H, $C_1$-$C_6$ alkyl, $C_3$-$C_6$ (hetero)cycloalkyl, $C_2$-$C_6$ alkenyl, $C_3$-$C_6$ (hetero)cycloalkenyl, $C_2$-$C_6$ alkynyl, $C_5$-$C_7$ (hetero)aryl, $C_6$-$C_{13}$ aralkyl, wherein alkyl, (hetero)cycloalkyl, aralkyl, alkenyl, (hetero)cycloalkenyl, alkynyl, and (hetero)aryl may be substituted by one or more substituents selected from F, CN, and optionally fluorinated oxiranyl;
$R^7$ is selected from $C_1$-$C_6$ alkyl, $C_3$-$C_6$ (hetero)cycloalkyl, $C_2$-$C_6$ alkenyl, $C_3$-$C_6$ (hetero)cycloalkenyl, $C_2$-$C_6$ alkynyl, $C_5$-$C_7$ (hetero)aryl, and $C_6$-$C_{13}$ aralkyl, wherein alkyl, (hetero)cycloalkyl, aralkyl, alkenyl, (hetero)cycloalkenyl, alkynyl, and (hetero)aryl may be substituted by one or more substituents selected from F, CN, $C_1$-$C_6$ alkyl, $C_2$-$C_6$ alkenyl, $C_5$-$C_7$ (hetero)aryl, $OR^9$, $OC(O)R^9$, $C(O)R^9$, $C(O)OR^9$, $OC(O)OR^9$, $OC(O)C(O)OR^9$, $S(O)_2OR^9$, $OS(O)_2R^9$, and $C_3$-$C_6$ (hetero)cycloalkyl which may be substituted by one or more substituents selected from $C_1$-$C_6$ alkyl, $C_3$-$C_6$ (hetero)cycloalkyl, $C_2$-$C_6$ alkenyl, $C_3$-$C_6$ (hetero)cycloalkenyl, $C_2$-$C_6$ alkynyl, $C_5$-$C_7$ (hetero)aryl, $C_6$-$C_{13}$ aralkyl, wherein alkyl, (hetero)cycloalkyl, aralkyl, alkenyl, (hetero)cycloalkenyl, alkynyl, and (hetero)aryl may be substituted by one or more substituents selected from F, CN, and optionally fluorinated oxiranyl;
$R^8$ and $R^9$ are independently from each other selected from H, $C_1$-$C_6$ alkyl, $C_3$-$C_6$ (hetero)cycloalkyl, $C_2$-$C_6$ alkenyl, $C_3$-$C_6$ (hetero)cycloalkenyl, $C_2$-$C_6$ alkynyl, $C_5$-$C_7$ (hetero)aryl, $C_6$-$C_{13}$ aralkyl, wherein alkyl, (hetero)cycloalkyl, aralkyl, alkenyl, (hetero)cycloalkenyl, alkynyl, and (hetero)aryl may be substituted by one or more substituents selected from F, CN, and optionally fluorinated oxiranyl; and
s and t are independently from each other 1, 2 or 3.

The term "$C_1$-$C_6$ alkyl" as used herein means a straight or branched saturated hydrocarbon group with 1 to 6 carbon atoms having one free valence and includes, e.g., methyl, ethyl, n-propyl, isopropyl, n-butyl, sec-butyl, isobutyl, tert-butyl, n-pentyl, iso-pentyl, 2,2-dimethylpropyl, n-hexyl, iso-hexyl, 2-ethyl hexyl, n-heptyl, iso-heptyl, n-octyl, iso-octyl, n-nonyl, n-decyl and the like. Preferred are $C_1$-$C_4$ alkyl groups and most preferred are 2-propyl, methyl and ethyl. The term "$C_1$-$C_4$ alkanediyl" as used herein denotes a straight or branched saturated hydrocarbon group with 1 to 4 carbon atoms and has two free valences. $C_1$-$C_4$ alkanediyl includes e.g. —$CH_2$—, —$CH_2CH_2$—, —$CH_2CH_2CH_2$—, —$CH_2CH_2CH_2CH_2$—, and —$CH_2CHCH_3$—, preferred is $C_1$-$C_3$ alkanediyl, more preferred are —$CH_2$— and —$CH_2CH_2$—.

The term "$C_3$-$C_6$ (hetero)cycloalkyl" as used herein means a cyclic saturated hydrocarbon group with 3 to 6 carbon atoms wherein the cycle has one free valence and wherein one or more C-atoms may be replaced by N, O or S. Examples of $C_3$-$C_6$ cycloalkyl include cyclopropyl, cyclobutyl, cyclopentyl and cyclohexyl, preferred is cyclohexyl. Examples of $C_3$-$C_6$ hetero cycloalkyl are oxiranyl and tetrahydrofuryl, preferred is oxiranyl (1,2-epoxy-ethyl).

The term "oxiranediyl" as used herein means a cyclic saturated hydrocarbon group containing two carbon atoms and one oxygen atom wherein the each C-atom has one free valence or one C-atom has two free valences.

The term "oxirane cycle" as used herein means a substituted or unsubstituted oxirane cycle and includes oxiranyl, 1,1-oxiranediyl, and 1,2-oxiranediyl.

The term "$C_2$-$C_6$ alkenyl" as used herein refers to an unsaturated straight or branched hydrocarbon group with 2 to 6 carbon atoms having one free valence. Unsaturated means that the alkenyl group contains at least one C—C double bond. $C_2$-$C_6$ alkenyl includes for example ethenyl, 1-propenyl, 2-propenyl, 1-n-butenyl, 2-n-butenyl, iso-butenyl, 1-pentenyl, 1-hexenyl and the like. Preferred are $C_2$-$C_4$ alkenyl groups and in particular ethenyl and 1-propen- 3-yl (allyl). The term "$C_2$-$C_4$ alkenediyl" as used herein refers to an unsaturated straight or branched hydrocarbon group with 2 to 4 carbon atoms which has two free valences and contains at least one CC double bond. $C_2$-$C_4$ alkenediyl includes e.g. —CH=CH—, —CH=CHCH$_2$—, —CH=CHCH$_2$CH$_2$—, —CH=CHCH(CH$_3$)—, —CH$_2$CH=CHCH$_2$—, and CH=CCH$_3$—, preferred are $C_2$-$C_3$ alkenyl, more preferred is CH=CH—, The term "$C_3$-$C_6$ (hetero)cycloalkenyl" as used herein refers to a cyclic unsaturated hydrocarbon group with 3 to 6 carbon atoms having one free valence wherein one or more C-atoms may be replaced by N, O or S. Unsaturated means that the cycloalkenyl group contains at least one CC double bond. Examples of $C_3$-$C_6$ (hetero)cycloalkenyl are cyclopropenyl, cyclobutenyl, cyclopentenyl, and cyclohexenyl.

The term "$C_2$-$C_6$ alkynyl" as used herein refers to an unsaturated straight or branched hydrocarbon group with 2 to 6 carbon atoms having one free valence, wherein the hydrocarbon group contains at least one C—C triple bond. $C_2$-$C_6$ alkynyl includes for example ethynyl, 1-propynyl, 2-propynyl, 1-n-butinyl, 2-n-butynyl, iso-butinyl, 1-pentynyl, 1-hexynyl and the like. Preferred is $C_2$-$C_4$ alkynyl, in particular 1-propyn-3-yl (propargyl). The term "$C_2$-$C_4$ alkynediyl" as used herein refers to an unsaturated straight or branched hydrocarbon group with 2 to 4 carbon atoms which has two free valences and contains at least one C—C triple bond. $C_2$-$C_4$ alkynyl includes for example —C≡C—, —C≡CCH$_2$—, —C≡CCH$_2$CH$_2$—, and —C≡CCH(CH$_3$)—, preferred is $C_2$-$C_3$ alkynyl, more preferred is —C≡C—.

The term "$C_5$-$C_7$ (hetero)aryl" as used herein denotes an aromatic 5- to 7-membered hydrocarbon cycle having one free valence, wherein one or more C-atom may be replaced by N, O or S. An example of $C_5$-$C_7$ aryl is phenyl, examples of $C_5$-$C_7$ heteroaryl are pyrrolyl, furanyl, thiophenyl, pyridinyl, pyranyl, and thiopyranyl.

The term "$C_7$-$C_{13}$ aralkyl" as used herein denotes an aromatic 5- to 7-membered hydrocarbon cycle substituted by one or more $C_1$-$C_6$ alkyl. The $C_7$-$C_{13}$ aralkyl group contains in total 7 to 13 C-atoms and has one free valence. The free valence may be located at the aromatic cycle or at a $C_1$-$C_6$ alkyl group, i.e. $C_7$-$C_{13}$ aralkyl group may be bound via the aromatic part or via the alkyl part of the aralkyl group. Examples of $C_7$-$C_{13}$ aralkyl are methylphenyl, 1,2-dimethylphenyl, 1,3-dimethylphenyl, 1,4-dimethylphenyl, ethylphenyl, 2-propylphenyl, and the like.

According to one embodiment of the present invention the at least one compound of formula (I) is selected from compounds of formula (I) wherein $R^1$ is C(O)O$R^7$. According to a further embodiment of the present invention the at least one compound of formula (I) is selected from compounds of formula (I) wherein $R^1$ is C(O)C(O)O$R^7$. In another embodiment of the invention the at least one compound of formula (I) is selected from compounds of formula (I) wherein $R^1$ is selected from S(O)$_2$$R^7$, S(O)$_2$O$R^7$, (CH$_2$)$_s$SO$_2$(CH$_2$)$_t$$R^7$, P(O)(O$R^7$)$R^7$, and P(O)(O$R^7$)$_2$. $R^2$, $R^3$, $R^4$, $R^5$ and $R^6$ are preferably independently from each other selected from H and $C_1$-$C_6$ alkyl, wherein alkyl may be substituted by one or more groups selected from F, CN and optionally fluorinated oxiranyl, more preferred they are independently from each other selected from H and $C_1$-$C_6$ alkyl, most preferred $R^2$, $R^3$, $R^4$, $R^5$ and $R^6$ are all hydrogen.

$R^7$ is preferably selected from $C_1$-$C_6$ alkyl, $C_3$-$C_6$ (hetero)cycloalkyl, $C_5$-$C_7$ (hetero)aryl, and $C_6$-$C_{13}$ aralkyl, wherein alkyl, aralkyl, and (hetero)aryl may be substituted by one or more substituents selected from F, CN, $C_1$-$C_6$ alkyl, $C_3$-$C_6$ (hetero)cycloalkyl, $C_2$-$C_6$ alkenyl, $C_5$-$C_7$ (hetero)aryl, more preferred $R^7$ contains at least one oxirane cycle, most preferred $R^7$ is 1,2-epoxy-propan-3-yl. In the case that a group contains more than one $R^7$, e.g. P(O)(O$R^7$)$R^7$, and P(O)(O$R^7$)$_2$, the more than one $R^7$ are selected independently from each other from the substituents described for $R^7$.

According to a further embodiment the compounds of formula (I) are selected from compounds of formula (I) wherein $R^2$, $R^3$, $R^4$, $R^5$ and $R^6$ are all hydrogen, $R^7$ is 1,2-epoxy-propan-3-yl and $R^1$ is selected from C(O)O$R^7$, C(O)C(O)O$R^7$, S(O)$_2$$R^7$, S(O)$_2$O$R^7$, (CH$_2$)$_s$SO$_2$(CH$_2$)$_t$$R^7$, P(O)(O$R^7$)$R^7$, and P(O)(O$R^7$)$_2$, preferably $R^1$ is C(O)C(O)O$R^7$.

According to another embodiment $R^2$, $R^3$, $R^4$, $R^5$ and $R^6$ are all hydrogen, $R^1$ is selected from S(O)$_2$$R^7$, S(O)$_2$O$R^7$, (CH$_2$)$_s$SO$_2$(CH$_2$)$_t$$R^7$, P(O)(O$R^7$)$R^7$, and P(O)(O$R^7$)$_2$, and $R^7$ is selected from $C_1$-$C_6$ alkyl, $C_3$-$C_6$ cycloalkyl, $C_5$-07 (hetero)aryl, and $C_6$-$C_{13}$ aralkyl, wherein alkyl, aralkyl, and (hetero)aryl may be substituted by one or more substituents selected from F, CN, $C_1$-$C_6$ alkyl, $C_3$-$C_6$ (hetero)cycloalkyl, $C_2$-$C_6$ alkenyl, $C_5$-$C_7$ (hetero)aryl.

Compounds of formula (I) may contain one oxirane cycle, the compounds of formula (I) may also contain at least two oxirane cycles, e.g. two or three oxirane cycles. Preferred compounds of formula (I) are those wherein $R^7$ contains at least one oxirane cycle. Especially preferred compounds of formula (I) wherein $R^7$ contains at least one oxirane cycle are compounds of the following formula (II)

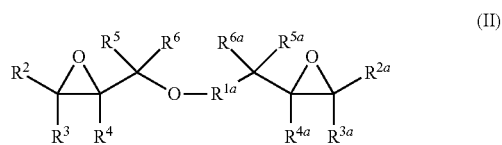

(II)

wherein
$R^{1a}$ is selected from —C(=O)—, —C(=O)O—, —C(=O)C(=O)O—, —C(=O)$R^{7a}$C(=O)O—, —S(O)$_2$—, —S(O)$_2$—, —S(O)$_2$O—, —(CH$_2$)$_s$SO$_2$(CH$_2$)$_t$O—, —P(O)(O$R^{7b}$)—, and —P(O)(O$R^{7b}$)O—;
$R^2$, $R^{2a}$, $R^3$, $R^{3a}$, $R^4$, $R^{4a}$, $R^5$, $R^{5a}$, $R^6$ and $R^{6a}$ are independently from each other selected from H, F, $C_1$-$C_6$ alkyl, $C_3$-$C_6$ (hetero)cycloalkyl, $C_2$-$C_6$ alkenyl, $C_3$-$C_6$ (hetero)cycloalkenyl, $C_2$-$C_6$ alkynyl, $C_5$-$C_7$ (hetero)aryl, $C_6$-$C_{13}$ aralkyl, wherein alkyl, (hetero)cycloalkyl, aralkyl, alkenyl, (hetero)cycloalkenyl, alkynyl, and (hetero)aryl may be substituted by one or more substituents selected from F, CN, and optionally fluorinated oxiranyl;
$R^{7a}$ is selected from $C_1$-$C_4$ alkanediyl, $C_2$-$C_4$ alkenediyl, $C_2$-$C_4$ alkynediyl and 1,2-oxiranediyl; and
$R^{7b}$ is selected from $C_1$-$C_6$ alkyl, $C_3$-$C_6$ (hetero)cycloalkyl, $C_2$-$C_6$ alkenyl, $C_3$-$C_6$ (hetero)cycloalkenyl, $C_2$-$C_6$ alkynyl, $C_5$-$C_7$ (hetero)aryl, $C_6$-$C_{13}$ aralkyl, wherein alkyl, (hetero)cycloalkyl, aralkyl, alkenyl, (hetero)cycloalkenyl, alkynyl, and (hetero)aryl may be substituted by one or more substituents selected from F, CN, and optionally fluorinated oxiranyl.
$R^{1a}$ is preferably selected from —C(=O)O—, —C(=O)C(=O)O—, —C(=O)$R^{7a}$C(=O)O—, S(O)$_2$—, —S(O)$_2$O—, —(CH$_2$)$_s$SO$_2$(CH$_2$)$_t$O—, —P(O)(O$R^{7b}$)—, and —P(O)(O$R^{7b}$)O—, more preferred $R^{1a}$ is selected from —C(=O)O—, —C(=O)C(=O)O—, and —C(=O)$R^{7a}$C(=O)O—, or from S(O)$_2$—, —S(O)$_2$O—, —(CH$_2$)$_s$SO$_2$(CH$_2$)$_t$O—, —P(O)(O$R^{7b}$)—, and —P(O)(O$R^{7b}$)O—.

$R^{7a}$ is preferably selected from —CH$_2$—, —CH$_2$CH$_2$—, —CH=CH—, —C≡C—, and 1,2-oxiranediyl, i.e.

Compounds of formula (II) are preferred wherein $R^2$, $R^3$, $R^4$, $R^5$, $R^6$, $R^{2a}$, $R^{3a}$, $R^{4a}$, $R^{5a}$ and $R^{6a}$ are selected from H and $C_1$-$C_6$ alkyl, wherein alkyl may be substituted by one or more groups selected from F, CN and optionally fluorinated oxiranyl, more preferred $R^2$, $R^3$, $R^4$, $R^5$, $R^6$, $R^{2a}$, $R^{3a}$, $R^{4a}$, $R^{5a}$ and $R^{6a}$ are independently from each other selected from H and $C_1$-$C_6$ alkyl, most preferred $R^2$, $R^3$, $R^4$, $R^5$, $R^6$, $R^{2a}$, $R^{3a}$, $R^{4a}$, $R^{5a}$ and $R^{6a}$ are all hydrogen.

Particular preferred compounds of formulae (I) and (II) are

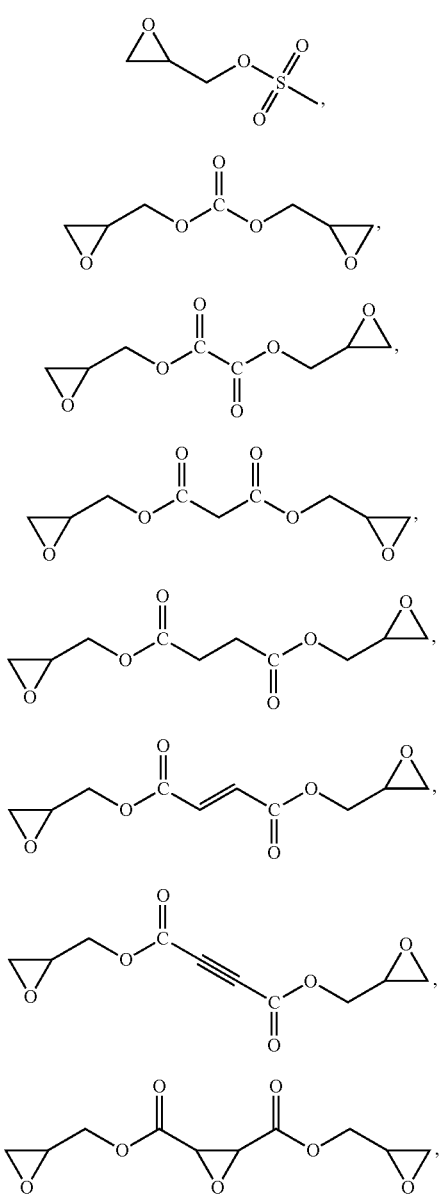

Compounds IIe and IIg exist in cis- and trans-form, both stereoisomers and mixtures of the respective stereoisomers are included by the present invention.

The concentration of the at least one compound of formula (I) in the inventive electrolyte composition (A) usually is 0.001 to 10 wt.-%, preferred 0.01 to 2.5 wt.-%, more preferred 0.01 to 2 wt.-% and most preferred 0.01 to 1.5 wt.-%, based on the total weight of the electrolyte composition (A).

The electrolyte composition (A) may contain at least one further additive (iv) which is selected from the group consisting of vinylene carbonate and its derivatives, vinyl ethylene carbonate and its derivatives, methyl ethylene carbonate and its derivatives, lithium (bisoxalato) borate, lithium difluoro (oxalato) borate, lithium tetrafluoro (oxalato) phosphate, lithium oxalate, 2-vinyl pyridine, 4-vinyl pyridine, cyclic exo-methylene carbonates, sultones, cyclic and acyclic sulfonates, cyclic and acyclic sulfites, cyclic and acyclic sulfinates, organic esters of inorganic acids, acyclic and cyclic alkanes having a boiling point at 1 bar of at least 36° C., and aromatic compounds, optionally halogenated cyclic and acyclic sulfonylimides, optionally halogenated cyclic and acyclic phosphate esters, optionally halogenated cyclic and acyclic phosphines, optionally halogenated cyclic and acyclic phosphites including, optionally halogenated cyclic and acyclic phosphazenes, optionally halogenated cyclic and acyclic silylamines, optionally halogenated cyclic and acyclic halogenated esters, optionally halogenated cyclic and acyclic amides, optionally halogenated cyclic and acyclic anhydrides, ionic liquids, and optionally halogenated organic heterocycles. The additive (iv) is preferably selected to be different from the compound selected as conducting salt (ii) present in the respective electrolyte composition (A). Preferably additive (iv) is also different from the at least one organic aprotic solvent (i) present in the respective electrolyte composition (A).

Preferred ionic liquids according to the present invention are selected from ionic liquids of formula [K]$^+$[L]$^-$ in which:

[K]$^+$ denotes a cation, preferably reduction-stable, selected from the cation groups of the general formulae (II) to (IX)

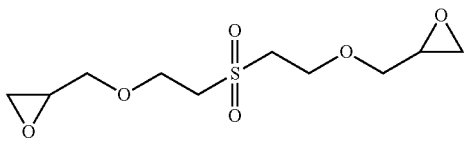

(IIh)

(II)

(III)

(IV)

(V)

-continued

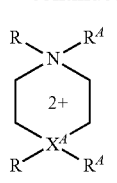
(VI)

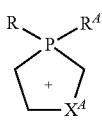
(VII)

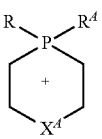
(VIII)

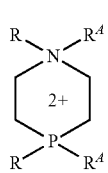
(IX)

wherein
R denotes H, $C_1$- to $C_6$-alkyl, $C_2$- to $C_6$-alkenyl, and phenyl, preferably methyl, ethyl, and propyl;
$R^A$ denotes —$(CH_2)_s$—O—C(O)—R, —$(CH_2)_s$—C(O)—OR, —$(CH_2)_s$—S(O)$_2$—OR, —$(CH_2)_s$—O—S(O)$_2$—R, —$(CH_2)_s$—O—S(O)$_2$—OR, —$(CH_2)_s$—O—C(O)—OR, —$(CH_2)_s$—HC=CH—R, —$(CH_2)_s$—CN,

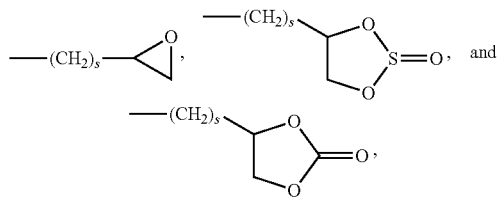

wherein individual $CH_2$ groups may be replaced by O, S or NR and s=1 to 8, preferably s=1 to 3;
$X^A$ denotes $CH_2$, O, S or $NR^B$;
$R^B$ denotes H, $C_1$- to $C_6$-alkyl, $C_2$- to $C_5$-alkenyl, phenyl, and —$(CH_2)_s$—CN with s=1 to 8, preferably s=1 to 3; preferably $R^B$ is methyl, ethyl, propyl or H;
and
$[L]^-$ denotes an anion selected from the group $BF_4^-$, $PF_6^-$, $[B(C_2O_4)_2]^-$, $[F_2B(C_2O_4)]^-$, $[N(S(O)_2F_2]^-$, $[F_pP(C_qF_{2q+1})_{6-p}]^-$, $[N(S(O)_2C_qF_{2q+1})_2]^-$, $[C_qF_{2q+1})_2P(O)O]^-$, $[C_qF_{2q+1}P(O)O_2]^{2-}$, $[OC(O)C_qF_{2q+1}]^-$, $[OS(O)_2C_qF_{2q+1}]^-$, $[N(C(O)C_qF_{2q+1})_2]^-$, $[N(C(O)C_qF_{2q+1})(S(O)_2C_qF_{2q+1})]^-$, $[N(C(O)C_qF_{2q+1})(C(O))F]^-$; $[N(S(O)_2C_qF_{2q+1})(S(O)_2F)]^-$; $[C(C(O)C_qF_{2q+1})_3]^-$, and $[C(S(O)_2C_qF_{2q+1})_3N(SO_2CF_3)_2]^-$;
wherein p is an integer in the range from 0 to 6 and q is an integer in the range from 1 to 20, preferably q is an integer in the ranger from 1 to 4.

Preferred ionic liquids for use as additive (iv) are ionic liquids of formula [K][L] in which [K] is selected from pyrrolidinium cations of formula (II) with X is $CH_2$ and s is an integer in the range of from 1 to 3 and [L] is selected from the group consisting of $BF_4^-$, $PF_6^-$, $[B(C_2O_4)_2]^-$, $[F_2B(C_2O_4)]^-$, $[N(S(O)_2F)_2]^-$, $[N(SO_2C_2F_5)_2^2]^-$, $[F_3P(C_2F_5)_3]^-$, and $[F_3P(C_4F_9)_3]^-$.

If one or more further additives (iv) are present in the electrolyte composition (A), the total concentration of further additives (iv) is at least 0.001 wt.-%, preferred 0.005 to 5 wt.-% and most preferred 0.01 to 2 wt.-%, based on the total weight of the electrolyte composition (A).

A further object of the present invention is the use of at least one compound of formula (I) as described above as additive for electrolytes in electrochemical cells, preferably in lithium ion secondary electrochemical cells.

The compounds of general formula (I) are well-suited as film forming additives in electrochemical cells. The film may be formed on the anode and/or on the cathode. Preferably the compounds of general formula (I) are used as film forming additives in lithium ion secondary electrochemical cells, in particular as additives forming a film on the anode of lithium ion secondary electrochemical cells.

The compounds of general formula (I) are usually added to the electrolyte composition to yield a concentration of from is 0.001 to 10 wt.-%, preferred 0.01 to 2 wt.-% and most preferred 0.01 to 1.5 wt.-%, based on the total weight of the electrolyte composition (A).

Another object of the present invention is an electrochemical cell comprising
(A) the electrolyte composition as described above,
(B) at least one cathode comprising at least one cathode active material, and
(C) at least one anode comprising at least one anode active material.

Preferably the electrochemical cell is a secondary lithium ion electrochemical cell, i.e. secondary lithium ion electrochemical cell comprising a cathode comprising a cathode active material that can reversibly occlude and release lithium ions and an anode comprising an anode active material that can reversibly occlude and release lithium ions. The terms "secondary lithium ion electrochemical cell" and "(secondary) lithium ion battery" are used interchangeably within the present invention.

The at least one cathode active material preferably comprises a material capable of occluding and releasing lithium ions selected from lithiated transition metal phosphates and lithium ion intercalating transition metal oxides.

Examples of lithiated transition metal phosphates are $LiCoPO_4$ and $LiFePO_4$, examples of lithium ion intercalating transition metal oxides are transition metal oxides with layered structure having the general formula (X) $Li_{(1+z)}[Ni_aCo_bMn_c]_{(1-z)}O_{2+e}$ wherein z is 0 to 0.3; a, b and c may be same or different and are independently 0 to 0.8 wherein a+b+c=1; and −0.1≤e≤0.1, and manganese-containing spinels of general formula (XI) $Li_{1+t}M_{2-t}O_{4-d}$ wherein d is 0 to 0.4, t is 0 to 0.4 and M is Mn and at least one further metal selected from the group consisting of Co and Ni, and $Li_{(1+g)}[Ni_hCo_iA_j]_{(1-g)}O_{2+k}$. Typical values for g, h, I, j and k are: g=0, h=0.8 to 0.85, i=0.15 to 0.20, j=0.02 to 0.03 and k=0.

In one preferred embodiment the cathode active material is selected from $LiCoPO_4$. The cathode containing $LiCoPO_4$ as cathode active material may also be referred to as $LiCoPO_4$ cathode. The $LiCoPO_4$ may be doped with Fe, Mn, Ni, V, Mg, Al, Zr, Nb, Tl, Ti, K, Na, Ca, Si, Sn, Ge, Ga, B, As, Cr, Sr, or rare earth elements, i.e., a lanthanide, scandium and yttrium. $LiCoPO_4$ with olivine structure is particularly suited according the present invention due to its high operating voltage (red-ox potential of 4.8 V vs. $Li/Li^+$), flat voltage profile and a high theoretical capacity of about 170 mAh/g. The cathode may comprise a $LiCoPO_4/C$ composite material. The preparation of a suited cathode comprising a LiCoPO$_4$/C composite material is described in Markevich et al., Electrochem. Comm., 2012, 15, 22-25.

In another preferred embodiment of the present invention the cathode active material is selected from transition metal oxides with layer structure having the general formula (X) Li$_{(1+z)}$[Ni$_a$Co$_b$Mn$_c$]$_{(1-z)}$O$_{2+e}$ wherein z is 0 to 0.3; a, b and c may be same or different and are independently 0 to 0.8 wherein a+b+c=1; and −0.1≤e≤0.1. Preferred are transition metal oxides with layer structure having the general formula (X) Li$_{(1+z)}$[Ni$_a$Co$_b$Mn$_c$]$_{(1-z)}$O$_{2+e}$ wherein z is 0.05 to 0.3, a=0.2 to 0.5, b=0 to 0.3 and c=0.4 to 0.8 wherein a+b+c=1; and −0.1≤e≤0.1. In one embodiment of the present invention, the transition metal oxides with layer structure of general formula (X) are selected from those in which [Ni$_a$Co$_b$Mn$_c$] is selected from Ni$_{0.33}$Co$_0$Mn$_{0.66}$, Ni$_{0.25}$Co$_0$Mn$_{0.75}$, Ni$_{0.35}$Co$_{0.15}$Mn$_{0.5}$, Ni$_{0.21}$Co$_{0.08}$Mn$_{0.71}$ and Ni$_{0.22}$Co$_{0.12}$Mn$_{0.66}$, in particular preferred are Ni$_{0.21}$Co$_{0.08}$Mn$_{0.71}$ and Ni$_{0.22}$Co$_{0.12}$Mn$_{0.66}$. The transition metal oxides of general formula (X) are also called High Energy NCM (HE-NCM) since they have higher energy densities than usual NCMs. Both HE-NCM and NCM have operating voltage of about 3.3 to 3.8 V against Li/Li$^+$, but high cut off voltages (>4.6 V) have to be used for charging HE-NCMS to actually accomplish full charging and to benefit from their higher energy density. According to a further preferred embodiment of the present invention the cathode active material is selected from manganese-containing spinels of general formula (XI) Li$_{1+l}$M$_{2-t}$O$_{4-d}$ wherein d is 0 to 0.4, t is 0 to 0.4 and M is Mn and at least one further metal selected from the group consisting of Co and Ni. An example of a suited manganese-containing spinel of general formula (XI) is LiNi$_{0.5}$Mn$_{1.5}$O$_{4-d}$. These spinels are also called HE (high energy)-spinels.

Many elements are ubiquitous. For example, sodium, potassium and chloride are detectable in certain very small proportions in virtually all inorganic materials. In the context of the present invention, proportions of less than 0.5% by weight of cations or anions are disregarded, i.e. amounts of cations or anions below 0.5% by weight are regarded as non-significant. Any lithium ion-containing transition metal oxide comprising less than 0.5% by weight of sodium is thus considered to be sodium-free in the context of the present invention. Correspondingly, any lithium ion-containing mixed transition metal oxide comprising less than 0.5% by weight of sulfate ions is considered to be sulfate-free in the context of the present invention.

The cathode may further comprise electrically conductive materials like electrically conductive carbon and usual components like binders. Compounds suited as electrically conductive materials and binders are known to the person skilled in the art. For example, the cathode may comprise carbon in a conductive polymorph, for example selected from graphite, carbon black, carbon nanotubes, graphene or mixtures of at least two of the aforementioned substances. In addition, the cathode may comprise one or more binders, for example one or more organic polymers like polyethylene, polyacrylonitrile, polybutadiene, polypropylene, polystyrene, polyacrylates, polyvinyl alcohol, polyisoprene and copolymers of at least two comonomers selected from ethylene, propylene, styrene, (meth)acrylonitrile and 1,3-butadiene, especially styrene-butadiene copolymers, and halogenated (co)polymers like polyvinlyidene chloride, polyvinly chloride, polyvinyl fluoride, polyvinylidene fluoride (PVdF), polytetrafluoroethylene, copolymers of tetrafluoroethylene and hexafluoropropylene, copolymers of tetrafluoroethylene and vinylidene fluoride and polyacrylnitrile.

Furthermore, the cathode may comprise a current collector which may be a metal wire, a metal grid, a metal web, a metal sheet, a metal foil or a metal plate. A suited metal foil is aluminum foil.

According to one embodiment of the present invention the cathode has a thickness of from 25 to 200 μm, preferably of from 30 to 100 μm, based on the whole thickness of the cathode without the thickness of the current collector.

The anode (C) comprised within the lithium ion secondary battery of the present invention comprises an anode active material that can reversibly occlude and release lithium ions. In particular carbonaceous material that can reversibly occlude and release lithium ions can be used as anode active material. Carbonaceous materials suited are crystalline carbon such as a graphite material, more particularly, natural graphite, graphitized cokes, graphitized MCMB, and graphitized MPCF; amorphous carbon such as coke, mesocarbon microbeads (MCMB) fired below 1500° C., and mesophase pitch-based carbon fiber (MPCF); hard carbon and carbonic anode active material (thermally decomposed carbon, coke, graphite) such as a carbon composite, combusted organic polymer, and carbon fiber.

Further anode active materials are lithium metal, or materials containing an element capable of forming an alloy with lithium. Non-limiting examples of materials containing an element capable of forming an alloy with lithium include a metal, a semimetal, or an alloy thereof. It should be understood that the term "alloy" as used herein refers to both alloys of two or more metals as well as alloys of one or more metals together with one or more semimetals. If an alloy has metallic properties as a whole, the alloy may contain a nonmetal element. In the texture of the alloy, a solid solution, a eutectic (eutectic mixture), an intermetallic compound or two or more thereof coexist. Examples of such metal or semimetal elements include, without being limited to, titanium (Ti), tin (Sn), lead (Pb), aluminum, indium (In), zinc (Zn), antimony (Sb), bismuth (Bi), gallium (Ga), germanium (Ge), arsenic (As), silver (Ag), hafnium (Hf), zirconium (Zr) yttrium (Y), and silicon (Si). Metal and semimetal elements of Group 4 or 14 in the long-form periodic table of the elements are preferable, and especially preferable are titanium, silicon and tin, in particular silicon. Examples of tin alloys include ones having, as a second constituent element other than tin, one or more elements selected from the group consisting of silicon, magnesium (Mg), nickel, copper, iron, cobalt, manganese, zinc, indium, silver, titanium (Ti), germanium, bismuth, antimony and chromium (Cr). Examples of silicon alloys include ones having, as a second constituent element other than silicon, one or more elements selected from the group consisting of tin, magnesium, nickel, copper, iron, cobalt, manganese, zinc, indium, silver, titanium, germanium, bismuth, antimony and chromium.

A further possible anode active material is silicon which is able to intercalate lithium ions. The silicon may be used in different forms, e.g. in the form of nanowires, nanotubes, nanoparticles, films, nanoporous silicon or silicon nanotubes. The silicon may be deposited on a current collector. The current collector may be a metal wire, a metal grid, a metal web, a metal sheet, a metal foil or a metal plate. Preferred the current collector is a metal foil, e.g. a copper foil. Thin films of silicon may be deposited on metal foils by any technique known to the person skilled in the art, e.g. by sputtering techniques. One possibility of preparing Si thin film electrodes are described in R. Elazari et al.; Electrochem. Comm. 2012, 14, 21-24. It is also possible to use a silicon/carbon composite as anode active material according to the present invention.

Other possible anode active materials are lithium ion intercalating oxides of Ti.

Preferably the anode active material present in the inventive lithium ion secondary battery is selected from carbonaceous material that can reversibly occlude and release lithium ions, particularly preferred the carbonaceous material that can reversibly occlude and release lithium ions is selected from crystalline carbon, hard carbon and amorphous carbon, in particular preferred is graphite. In another preferred embodiment the anode active material present in the inventive lithium ion secondary battery is selected from silicon that can reversibly occlude and release lithium ions, preferably the anode comprises a thin film of silicon or a silicon/carbon composite. In a further preferred embodiment the anode active material present in the inventive lithium ion secondary battery is selected from lithium ion intercalating oxides of Ti.

The anode and cathode may be made by preparing an electrode slurry composition by dispersing the electrode active material, a binder, optionally a conductive material and a thickener, if desired, in a solvent and coating the slurry composition onto a current collector. The current collector may be a metal wire, a metal grid, a metal web, a metal sheet, a metal foil or a metal plate. Preferred the current collector is a metal foil, e.g. a copper foil or aluminum foil.

The inventive lithium ion batteries may contain further constituents customary per se, for example separators, housings, cable connections etc. The housing may be of any shape, for example cuboidal or in the shape of a cylinder, the shape of a prism or the housing used is a metal-plastic composite film processed as a pouch. Suited separators are for example glass fiber separators and polymer-based separators like polyolefin separators.

Several inventive lithium ion batteries may be combined with one another, for example in series connection or in parallel connection. Series connection is preferred. The present invention further provides for the use of inventive lithium ion batteries as described above in devices, especially in mobile devices. Examples of mobile devices are vehicles, for example automobiles, bicycles, aircraft, or water vehicles such as boats or ships. Other examples of mobile devices are those which are portable, for example computers, especially laptops, telephones or electrical power tools, for example from the construction sector, especially drills, battery-driven screwdrivers or battery-driven staplers. But the inventive lithium ion batteries can also be used for stationary energy stores.

The invention is illustrated by the examples which follow, which do not, however, restrict the invention.

1. Preparation of Compounds

Preparation of Diglycidyl Oxylate (Compound 1)

Diglycidyl oxalate 1 was prepared according to the following literature procedure:

New reaction of glycidols with oxalyl chloride and phosgene—an approach to cyclic esters. Bredikhin, A. A.; Pashagin, A. V.; Strunskaya, E. I.; Gubaydullin, A. T.; Litvinov, I. A.; Bredikhina, Z. A. A. E. Arbuzov, Russian Chemical Bulletin 1999, 48(11), 2086-2090.

Preparation of oxiran-2-yl methyl methansulfonate (compound 2)

To a stirred solution of glycidol (1 equiv) in dry ethyl acetate was added triethyl amine (1,5 equiv) and catalytic quantities of DMAP. After cooling down to −5° C. methanesulfonic acid anhydride (1.1 equiv) was added portion wise. The mixture was stirred at ambient temperature for few hours until complete conversion was achieved (GC-Analysis). The crude material was isolated after aqueous work up and purified by distillation.

Preparation of bicyclo[2.2.2]oct-5-ene-2-carboxylic acid-2-oxiranylmethyl ester (compound 3, comparative)

A solution of 5.37 g (65 mmol) 1,3-cyclohexadiene and 7.72 g (60.26 mmol) glycidylacrylate in 60 ml of toluene was stirred at 135° C. for 24 h. After this time, the reaction mixture was allowed to cool down to room temperature. After removal of the toluene the crude product mixture was worked up by distillation (50° C., 8 mbar). Compound 3 was obtained as a colorless liquid. Yield: 89%.

Preparation of 2,2"-di(glycidyloxyethyl) sulfone (compound 4)

A vessel was charged with divinylsulfone (20 g, 0.17 mol) and a 25 weight-% solution of NaOCH$_3$ in methanol (0.23 g, 1.06 mmol) and heated to 80° C. Glycidol (25 g, 0.34 mol) was then added and the reaction stirred for 20 min at 90° C. After cooling down to room temperature, the solution was neutralized with an excess of solid CO$_2$ (5 g) and the residue was purified via column chromatography on silica gel (eluent: cyclohexane/ethyl acetate 1/1.5) to give 32 g (0.12 mol) of the desired product (yield: 71%) as a yellow oil.

Compounds 1 to 4 are summarized in Table 1.

TABLE 1

Formulae of some compounds according to general formula (I)

| Compound | Name | Structure |
|---|---|---|
| 1 | Diglycidyl oxalate | 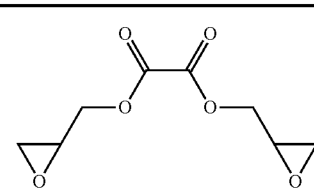 |

TABLE 1-continued

Formulae of some compounds according to general formula (I)

| Compound | Name | Structure |
|---|---|---|
| 2 | Oxiran-2-yl methyl methansulfonate | 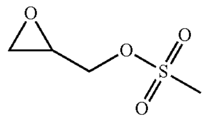 |
| 3 | | 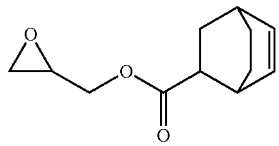 [SMILES: O=C(OCC1CO1)C1CC2C=CC1CC2] |
| 4 | 2,2'-di(glycidyloxyethyl) sulfone | 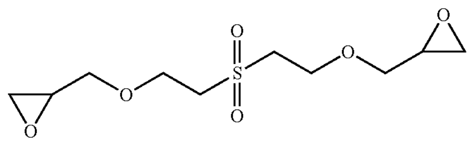 [SMILES: O=S(=O)(CCOCC1CO1)CCOCC1CO1] |

2. Electrochemical Cells

The additives were investigated towards film formation in coin cells (half cells). Graphite-coated tapes (2.2 mAh/g) and metal lithium were used as electrodes. A glass-fiber filter separator (Whatmann GF/D) was used as the separator, which was soaked with 120 µl electrolyte. Coin type half cells (type 2032—Hohsen) were prepared with $LiPF_6$, which was dissolved in a 3:7 mixture of ethylene carbonate/ethylmethyl carbonate yielding a 1 M $LiPF_6$ solution (base electrolyte composition). 2 wt.-% of additive was added to the electrolyte mixture. All cells were assembled in an argon-filled glove box (Unilab, MBraun) having oxygen and water levels below 10 ppm. Afterwards the test cells were transferred to a battery test station. Electrochemical cycling was done using a Maccor battery test system. The half cells were initially held at open circuit potential for 6 hours and the graphite anodes were subsequently lithiated until the cell voltage reached 0.025 V. Afterwards the graphite anodes were delithiated until the cell voltage had a value of 1.5 V. This test was performed at 0.01 C rate. Measurements were carried out at room temperature (25° C.).

The reduction potentials obtained from differential capacity vs. voltage plots of coin cells (Li/graphite) containing the base electrolyte composition with and without 2 wt.-% electrolyte additive are summarized in Table 2.

Corresponding electrolyte additives were further investigated in full cells at ambient temperature (25° C.) and at 45° C. The coin type cell contains a stainless steel spacer to contact the graphite anode and a stainless steel casing bottom to contact the backside of the cathode. The cathode material NCM 111 ($LiNi_{0.33}Co_{0.33}Mn_{0.33}O_2$) was used to make cathode tapes with a capacity of 2 $mAh/cm^2$. Graphite-coated tapes (capacity 2.2 $mAh/cm^2$) were used as anodes. A glass-fiber filter separator (Whatmann GF/D) was used as the separator, which was soaked with 120 µl electrolyte. Coin type full cells were prepared with $LiPF_6$ (Kanto Denka Koyo Co. Ltd), which was dissolved in a 3:7 mixture of ethylene carbonate/ethyl-methylcarbonate yielding a 1 M $LiPF_6$ solution. 0.5 wt.-% of additive was added to the electrolyte mixture. All cells were assembled in an argon-filled glove box (Unilab, MBraun) having oxygen and water levels below 10 ppm. Afterwards the test cells were transferred to a battery test station. Electrochemical cycling (charging/discharging) was done using a Maccor battery test system.

For the measurements at 25° C. the full cells were initially held at open circuit potential for 6 hours and subsequently charged to 4.2 V. Afterwards the cells were discharged to a low voltage cutoff of 3.0 V. The first two cycles were performed at 0.1 C rate followed by cycling at 0.5 C (10 cycles), rate test up to 10 C and continuous cycling at 1 C. All measurements were carried out in climate chambers. The internal resistance was determined by DC (discharge) pulse method (10 sec at 0.1 C, 10 sec at 1 C). The cell capacities obtained after 100 cycles and internal resistance values after 100 cycles of the NCM 111/graphite full cells are summarized in Table 2. The initial capacity of the cells was about 3.3 mAh.

TABLE 2

Test results

| Compound | Reduction potential (V vs Li/Li+) [V] | Capacity after 100 cycles [mAh] | Internal resistance after 100 cycles [Ω $cm^2$] |
|---|---|---|---|
| | 1.85 | 134.4 | 33.4 |
| | 0.85 | 134.6 | 34.13 |
| none | 0.78 | 134.7 | 35.8 |

TABLE 2-continued

Test results

| Compound | Reduction potential (V vs Li/Li$^+$) [V] | Capacity after 100 cycles [mAh] | Internal resistance after 100 cycles [Ω cm$^2$] |
|---|---|---|---|
| [norbornene epoxide ester structure] | 1.28 V | 117.3 | 76.6 |

The inventive electrolyte compositions show lower internal resistances in comparison to a similar electrolyte composition containing no compound of formula (I) and have a higher reduction potential indicating the film formation on the anode. The reduction peak observed for the base electrolyte composition containing no additive is significantly reduced for the inventive electrolyte compositions.

For the measurements at 45° C. the full cells were initially held at open circuit potential for 2 hours and subsequently charged to 4.2 V. Afterwards the cells were discharged to a low voltage cutoff of 3.0 V. The cells were cycled as follows: 1 cycle at 0.1 C, 1 cycle at 0.2 C, 10 cycles at 0.5 C followed by a rate test up to 4 C and continuous cycling at 1 C. The first 25 cycles were carried for conditioning the cells at room temperature (25° C.). After the conditioning period all cells were transferred to a climate chamber operated at 45° C. and cycling (1 C, 3.0-4.2 V) resumed at 45° C. The discharge capacities after 30 and 250 cycles at 45° C. for the base electrolyte composition and base electrolyte composition containing 0.5 wt.-% of compounds 2 and 4, respectively, are summarized in Table 3.

Electrochemical Tests with On-Line Mass Spectrometer

The electrolyte additive oxiran-2-yl methylmethansulfonate (compound 2 according to Table 1, "OMS") was further investigated by On-Line Mass Spectrometer analysis. The set up enables quantitative gas evolution analysis with a sealed battery design, applied to the study of the ethylene gas evolution during the 1$^{st}$ charging processes of a graphite anode. A detailed description of the system is given in N. Tsiouvaras et al., A Novel On-Line Mass Spectrometer Design for the Study of Multiple Charging Cycles of a Li—O$_2$ Battery, Journal of The Electrochemical Society, 160 (3) A471-A477 (2013). The size of the test cell was 9.5 ml.

The working electrode consisted of TIMCAL graphite SLP30 and 10 wt % PVdF (6.8 mg$_{SLP}$/cm$^2$, thickness—96 μm, support—Celgard C480). Li metal (half-cell arrangement) was used as counter electrode. 1 M LiPF$_6$ in EC/EMC (3:7 by volume) was used as comparison electrolyte mixture. Different amounts of OMS (0.5 or 2 wt. %) were added to the comparison electrolyte mixture. The working cell compartments and counter cell compartments were separated by a solid electrolyte barrier (Li$^+$-conducting glass ceramic, Ohara, Japan). Each test cell was held at open circuit voltage for 2 hours to allow system equilibration. Afterwards a cyclic voltammetry scan (0.5 mV/s) to 0 V vs. Li/Li$^+$ followed. During the next step the cell voltage was increased to 1.5 V vs. Li/Li$^+$ at a scan rate of 0.5 mV/s. The concentrations of gases in the cell atmosphere, in particular ethylene, were analyzed by an online mass spectrometer that was directly connected to the battery test cell through a calibrated capillary leak. The results obtained for the different electrolyte mixtures are summarized in Table 4.

TABLE 4

Amount of evolved ethylene during the 1$^{st}$ charging processes observed for different electrolyte mixtures

| Experiment No. | electrolyte | C$_2$H$_4$ evolution [ppm] during 1$^{st}$ cycle charge |
|---|---|---|
| C-4.1 | 1M LiPF$_6$ in EC/EMC (3:7) | 2,200 |
| 4.2 | 1M LiPF$_6$ in EC/EMC (3:7) + 0.5% by weight of compound 2 | 1,250 |

TABLE 3 base electrolyte composition with and without 0.5 wt.-% electrolyte additive at 45° C.

| Compound | Discharge capacity after 30 cycles at 45° C. [mAh/g] | Discharge capacity after 250 cycles at 45° C. [mAh/g] | Capacity retention during cycling at 45° C. [%] |
|---|---|---|---|
| none | 144.3 | 128.0 | 88.7 |
| [glycidyl methanesulfonate structure] | 144.6 | 130.8 | 90.4 |
| [bis-glycidyl ether sulfone structure] | 143.7 | 130.8 | 91 |

The capacity retention is the ratio of the discharge capacity after 250 cycles and after 30 cycles at 45° C.

TABLE 4-continued

Amount of evolved ethylene during the 1$^{st}$ charging processes observed for different electrolyte mixtures

| Experiment No. | electrolyte | C$_2$H$_4$ evolution [ppm] during 1$^{st}$ cycle charge |
|---|---|---|
| 4.3 | 1M LiPF$_6$ in EC/EMC (3:7) + 2% by weight of compound 2 | 800 |

In this context, ppm are volume-ppm and refer to the volume of the whole cell, 9.5 ml.

Electrochemical cells operated with electrolytes containing compound 2 displayed a significantly reduced evolution of ethylene during the first cycle compared to electrochemical cells operated with compound 2-free electrolytes.

The invention claimed is:

1. An electrolyte composition (A) comprising:
 (i) an aprotic organic solvent;
 (ii) a conducting salt;
 (iii) a compound of formula (I)

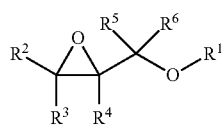

(I)

wherein
 R$^1$ is selected from the group consisting of C(O)C(O)OR$^7$, S(O)$_2$R$^7$, S(O)$_2$OR$^7$, (CH$_2$)$_s$SO$_2$(CH$_2$)$_t$R$^7$, P(O)(OR$^7$)R$^7$, and P(O)(OR$^7$)$_2$;
 R$^2$ is selected from the group consisting of H, F, C$_1$-C$_6$ alkyl, C$_3$-C$_6$ (hetero)cycloalkyl, C$_2$-C$_6$ alkenyl, C$_3$-C$_6$ (hetero)cycloalkenyl, C$_2$-C$_6$ alkynyl, C$_5$-C$_7$ (hetero)aryl, and C$_6$-C$_{13}$ aralkyl, wherein alkyl, (hetero)cycloalkyl, aralkyl, alkenyl, (hetero)cycloalkenyl, alkynyl, and (hetero)aryl may be substituted by one or more substituents selected from the group consisting of F, CN, C$_1$-C$_6$ alkyl, C$_3$-C$_6$ (hetero)cycloalkyl, C$_2$-C$_6$ alkenyl, C$_5$-C$_7$ (hetero)aryl, OR$^8$, C(O)R$^8$, C(O)OR$^8$, OC(O)R$^8$, OC(O)OR$^8$, OC(O)C(O)OR$^8$, S(O)$_2$R$^8$ and OS(O)$_2$R$^8$;
 R$^3$ and R$^4$ are each independently selected from the group consisting of H, F, C$_1$-C$_6$ alkyl, C$_3$-C$_6$ (hetero)cycloalkyl, C$_2$-C$_6$ alkenyl, C$_3$-C$_6$ (hetero)cycloalkenyl, C$_2$-C$_6$ alkynyl, C$_5$-C$_7$ (hetero)aryl, and C$_6$-C$_{13}$ aralkyl, wherein alkyl, (hetero)cycloalkyl, alkenyl, (hetero)cycloalkenyl, alkynyl, (hetero)aryl, and aralkyl, may be substituted by one or more substituents selected from the group consisting of F, CN, and optionally fluorinated oxiranyl;
 R$^5$ and R$^6$ are each independently selected from the group consisting of H, C$_1$-C$_6$ alkyl, C$_3$-C$_6$ (hetero)cycloalkyl, C$_2$-C$_6$ alkenyl, C$_3$-C$_6$ (hetero)cycloalkenyl, C$_2$-C$_6$ alkynyl, C$_5$-C$_7$ (hetero)aryl, and C$_6$-C$_{13}$ aralkyl, wherein alkyl, (hetero)cycloalkyl, aralkyl, alkenyl, (hetero)cycloalkenyl, alkynyl, and (hetero)aryl may be substituted by one or more substituents selected from the group consisting of F, CN, and optionally fluorinated oxiranyl;
 R$^7$ is selected from the group consisting of C$_1$-C$_6$ alkyl, C$_3$-C$_6$ (hetero)cycloalkyl, C$_2$-C$_6$ alkenyl, C$_3$-C$_6$ (hetero)cycloalkenyl, C$_2$-C$_6$ alkynyl, C$_5$-C$_7$ (hetero)aryl, and C$_6$-C$_{13}$ aralkyl, wherein alkyl, (hetero)cycloalkyl, aralkyl, alkenyl, (hetero)cycloalkenyl, alkynyl, and (hetero)aryl may be substituted by one or more substituents selected from the group consisting of F, CN, C$_1$-C$_6$ alkyl, C$_2$-C$_6$ alkenyl, C$_5$-C$_7$ (hetero)aryl, OR$^9$, OC(O)R$^9$, C(O)R$^9$, C(O)OR$^9$, OC(O)OR$^9$, OC(O)C(O)OR$^9$, S(O)$_2$OR$^9$, OS(O)$_2$R$^9$, and C$_3$-C$_6$ (hetero)cycloalkyl which may be substituted by one or more substituents selected from the group consisting of F, C$_1$-C$_6$ alkyl, C$_3$-C$_6$ (hetero)cycloalkyl, C$_2$-C$_6$ alkenyl, C$_3$-C$_6$ (hetero)cycloalkenyl, C$_2$-C$_6$ alkynyl, C$_5$-C$_7$ (hetero)aryl, and C$_6$-C$_{13}$ aralkyl, wherein alkyl, (hetero)cycloalkyl, aralkyl, alkenyl, (hetero)cycloalkenyl, alkynyl, and (hetero)aryl may be substituted by one or more substituents selected from the group consisting of F, CN, and optionally fluorinated oxiranyl;
 R$^8$ and R$^9$ are each independently selected from the group consisting of H, C$_1$-C$_6$ alkyl, C$_3$-C$_6$ (hetero)cycloalkyl, C$_2$-C$_6$ alkenyl, C$_3$-C$_6$ (hetero)cycloalkenyl, C$_2$-C$_6$ alkynyl, C$_5$-C$_7$ (hetero)aryl, and C$_6$-C$_{13}$ aralkyl, wherein alkyl, (hetero)cycloalkyl, aralkyl, alkenyl, (hetero)cycloalkenyl, alkynyl, and (hetero)aryl may be substituted by one or more substituents selected from the group consisting of F, CN, and optionally fluorinated oxiranyl;
 wherein s and t are independently from each other 1, 2, or 3; and
 (iv) optionally a further additive.

2. The electrolyte composition (A) according to claim 1 wherein R$^1$ is C(O)C(O)OR$^7$.

3. The electrolyte composition (A) according to claim 1 wherein R$^1$ is selected from the group consisting of S(O)$_2$R$^7$, S(O)$_2$OR$^7$, (CH$_2$)$_m$SO$_2$(CH$_2$)$_n$R$^7$, wherein m and n are independently from each other 1, 2, or 3, P(O)(OR$^7$)R$^7$, and P(O)(OR$^7$)$_2$.

4. The electrolyte composition (A) according to claim 1, wherein the compound of formula (I) comprises at least two oxirane cycles.

5. The electrolyte composition (A) according to claim 1, wherein R$^7$ comprises an oxirane cycle.

6. The electrolyte composition (A) according to claim 1, wherein the compound of formula (I) has a formula (II)

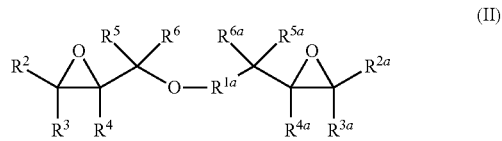

(II)

wherein
 R$^{1a}$ is selected from the group consisting of —C(=O)—, —C(=O)O—, —C(=O)C(=O)O—, —C(=O)R$^{7a}$C(=O)O—, —S(O)$_2$—, —S(O)$_2$O—, —(CH$_2$)$_s$SO$_2$(CH$_2$)$_t$O—, —P(O)(OR$^{7b}$)—, and —P(O)(OR$^{7b}$)O—;
 R$^2$, R$^{2a}$, R$^3$, R$^{3a}$, R$^4$, R$^{4a}$, R$^5$, R$^{5a}$, R$^6$ and R$^{6a}$ are each independently selected from the group consisting of H, F, C$_1$-C$_6$ alkyl, C$_3$-C$_6$ (hetero)cycloalkyl, C$_2$-C$_6$ alkenyl, C$_3$-C$_6$ (hetero)cycloalkenyl, C$_2$-C$_6$ alkynyl, C$_5$-C$_7$ (hetero)aryl, and C$_6$-C$_{13}$ aralkyl, wherein alkyl, (hetero)cycloalkyl, aralkyl, alkenyl, (hetero)cycloalkenyl, alkynyl, and (hetero)aryl may be substituted by one or more substituents selected from the group consisting of F, CN, and optionally fluorinated oxiranyl;
 R$^{7a}$ is selected from the group consisting of C$_1$-C$_4$ alkanediyl, C$_2$-C$_4$ alkenediyl, C$_2$-C$_4$ alkynediyl and 1,2-oxiranediyl;

$R^{7b}$ is selected from the group consisting of $C_1$-$C_6$ alkyl, $C_3$-$C_6$ (hetero)cycloalkyl, $C_2$-$C_6$ alkenyl, $C_3$-$C_6$ (hetero)cycloalkenyl, $C_2$-$C_6$ alkynyl, $C_5$-$C_7$ (hetero)aryl, and $C_6$-$C_{13}$ aralkyl, wherein alkyl, (hetero)cycloalkyl, aralkyl, alkenyl, (hetero)cycloalkenyl, alkynyl, and (hetero)aryl may be substituted by one or more substituents selected from the group consisting of F, CN, and optionally fluorinated oxiranyl, and wherein s and t are independently from each other 1, 2, or 3.

7. The electrolyte composition (A) according to claim 1, wherein the aprotic organic solvent (i) is selected from the group consisting of:
   (a) a cyclic or noncyclic organic carbonate, which may be partly halogenated,
   (b) a di-$C_1$-$C_{10}$-alkylether, which may be partly halogenated,
   (c) a di-$C_1$-$C_4$-alkyl-$C_2$-$C_6$-alkylene ether or polyether, which may be partly halogenated,
   (d) a cyclic ether, which may be partly halogenated,
   (e) a cyclic or acyclic acetal or ketal, which may be partly halogenated,
   (f) an orthocarboxylic acid ester, which may be partly halogenated,
   (g) a cyclic or noncyclic ester of a carboxylic acid, which may be partly halogenated,
   (h) a cyclic or noncyclic sulfone, which may be partly halogenated,
   (i) a cyclic or noncyclic nitrile or dinitrile, which may be partly halogenated, and
   (j) an ionic liquid, which may be partly halogenated.

8. The electrolyte composition (A) according to claim 1, wherein the conducting salt (ii) is selected from the group consisting of
   $Li[F_{6-x}P(C_yF_{2y+1})_x]$, wherein x is an integer in the range from 0 to 6 and y is an integer in the range from 1 to 20;
   $Li[B(R^9)_4]$, $Li[B(R^9)_2(OR^{10}O)]$ and $Li[B(OR^{10}O)_2]$ wherein each $R^9$ is independently selected from the group consisting of F, Cl, Br, I, $C_1$-$C_4$ alkyl, $C_2$-$C_4$ alkenyl, and $C_2$-$C_4$ alkynyl, wherein alkyl, alkenyl, and alkynyl may be substituted by one or more $OR^{11}$, wherein $R^{11}$ is selected from the group consisting of $C_1$-$C_6$ alkyl, $C_2$-$C_6$ alkenyl, and $C_2$-$C_6$ alkynyl, and ($OR^{10}O$) is a bivalent group derived from a 1,2- or 1,3-diol, a 1,2- or 1,3-dicarboxlic acid or a 1,2- or 1,3-hydroxycarboxylic acid, wherein the bivalent group forms a 5- or 6-membered cycle via both oxygen atoms with the central B-atom;
   $LiClO_4$; $LiAsF_6$; $LiCF_3SO_3$; $Li_2SiF_6$; $LiSbF_6$; $LiAlC_4$; $Li[N(SO_2F)_2]$; lithium tetrafluoro (oxalato) phosphate; lithium oxalate; and
   a salt of formula $Li[X(C_nF_{2n+1}SO_2)_m]$, where m and n are defined as follows:
   m=1 when X is oxygen or sulfur,
   m=2 when X is nitrogen or phosphorus,
   m=3 when X is carbon or silicon, and
   n is an integer in the range from 1 to 20.

9. The electrolyte composition (A) according to claim 1, comprising at least one further additive (iv) selected from the group consisting of vinylene carbonate, a derivative of vinylene carbonate, vinyl ethylene carbonate, a derivative of vinyl ethylene carbonate, methyl ethylene carbonate, a derivative of methyl ethylene carbonate, lithium (bisoxalato) borate, lithium difluoro (oxalato) borate, lithium tetrafluoro (oxalato) phosphate, lithium oxalate, 2-vinyl pyridine, 4-vinyl pyridine, a cyclic exo-methylene carbonate, a sultone, an organic ester of an inorganic acid, an acyclic or cyclic alkane having a boiling point at 1 bar of at least 36° C., and an aromatic compound, an optionally halogenated cyclic or acyclic sulfonylimide, an optionally halogenated cyclic or acyclic phosphate ester, an optionally halogenated cyclic or acyclic phosphine, an optionally halogenated cyclic or acyclic phosphite, an optionally halogenated cyclic or acyclic phosphazene, an optionally halogenated cyclic or acyclic silylamine, an optionally halogenated cyclic or acyclic halogenated ester, an optionally halogenated cyclic or acyclic amide, an optionally halogenated cyclic or acyclic anhydride, an ionic liquid and an optionally halogenated organic heterocycle.

10. The electrolyte composition (A) according to claim 1, wherein the concentration of the compound of formula (I) is 0.001 to 10 wt.-% based on a total weight of the electrolyte composition (A).

11. An electrochemical cell comprising
   (A) the electrolyte composition according to claim 1,
   (B) a cathode comprising a cathode active material, and
   (C) an anode comprising an anode active material.

12. The electrochemical cell according to claim 11, wherein the electrochemical cell is a secondary lithium ion battery.

* * * * *